(12) United States Patent
Gagnadre et al.

(10) Patent No.: US 7,384,398 B2
(45) Date of Patent: Jun. 10, 2008

(54) DEVICE AND METHOD FOR DETECTING ABNORMAL SITUATIONS

(75) Inventors: Claude Gagnadre, Ploemeur (FR); Michel Billon, Lannion (FR); Philippe Cosquer, Trebeurden (FR); Pierre Lutzler, Savines Lelac (FR); Odile Faraldi, Le Meux (FR); Sandrine Thuillier, Lorient (FR); Michel Valette, Trebeurden (FR); Helene Vinesse, Lannion (FR); Henry L'Her, Tregastel (FR); Olivier Sentieys, Louannec (FR)

(73) Assignee: Universite de Rennes, Rennes (FR)

( * ) Notice: Subject to any disclaimer, the term of this patent is extended or adjusted under 35 U.S.C. 154(b) by 0 days.

(21) Appl. No.: 10/275,357

(22) PCT Filed: May 4, 2001

(86) PCT No.: PCT/FR01/01375
§ 371 (c)(1), (2), (4) Date: Feb. 7, 2003

(87) PCT Pub. No.: WO01/85025
PCT Pub. Date: Nov. 15, 2001

(65) Prior Publication Data
US 2003/0153836 A1 Aug. 14, 2003

(30) Foreign Application Priority Data
May 5, 2000 (FR) ................... 00 05822

(51) Int. Cl.
*A61B 5/02* (2006.01)
*A61B 5/103* (2006.01)
*A61B 5/00* (2006.01)

(52) U.S. Cl. .............. 600/483; 600/485; 600/481; 600/587; 600/300; 600/301

(58) Field of Classification Search ............... 600/481, 600/483–485, 490–503, 300, 301, 549, 529, 600/534, 537, 538, 587, 595, 586, 561; 607/19–23
See application file for complete search history.

(56) References Cited

U.S. PATENT DOCUMENTS

| | | | | |
|---|---|---|---|---|
| 3,584,618 A | * | 6/1971 | Reinhard et al. | 600/536 |
| 4,765,340 A | * | 8/1988 | Sakai et al. | 600/324 |
| 5,197,489 A | * | 3/1993 | Conlan | 600/595 |
| 5,228,449 A | * | 7/1993 | Christ et al. | 600/504 |
| 5,515,858 A | | 5/1996 | Myllymäki | |
| 5,746,203 A | * | 5/1998 | Hood, Jr. | 600/300 |
| 5,964,720 A | * | 10/1999 | Pelz | 600/595 |
| 6,160,478 A | * | 12/2000 | Jacobsen et al. | 340/539.12 |
| 6,208,251 B1 | * | 3/2001 | Cadet et al. | 340/573.1 |
| 6,221,010 B1 | * | 4/2001 | Lucas | 600/300 |

FOREIGN PATENT DOCUMENTS

| | | |
|---|---|---|
| EP | 0 877 346 A1 | 11/1998 |
| FR | 2 785 073 | 10/1999 |
| GB | 2 312 309 A | 10/1997 |
| JP | 04285529 A * | 10/1992 |
| WO | WO 9829852 A1 * | 7/1998 |

* cited by examiner

*Primary Examiner*—Charles A. Marmor, II
*Assistant Examiner*—Navin Natnithithadha
(74) *Attorney, Agent, or Firm*—Steven M. Koehler; Westman, Champlin & Kelly, P.A.

(57) ABSTRACT

The invention concerns a device for detecting abnormal situations, in particular falls, in a living being, comprising means generating an alarm signal representing an abnormal situation, based on analysis of at least an activity information and, at least in some cases, at least a physiological information.

40 Claims, 6 Drawing Sheets

DEVICE AND METHOD FOR DETECTING ABNORMAL SITUATIONS

CROSS-REFERENCE TO RELATED APPLICATION

This Application is a Section 371 National Stage Application of International Application No. PCT/FR01/01375 filed May 4, 2001 and published as WO 01/85025 on Nov. 15, 2001, not in English.

FIELD OF THE INVENTION

The invention relates to the field of detecting certain abnormal situations, mainly pathological, falls in particular, in a human being. The particular aim of such detection is the transmission of an alarm to a third person (individual entity or services . . . ) carrying out a remote monitoring function.

BACKGROUND OF THE INVENTION

The invention can find applications in many situations, and can, in particular, equip elderly persons and/or those with reduced mobility, isolated workers, children, animals . . .

In prior art, remote alarm systems are generally constituted of an assembly worn by the subject and linked to a fixed base, for example by an HF link. In the event of an abnormal situation, the fixed base transmits a coded message, carried for example by the telephone network, towards a specialised centre. In some institutions, the message can be carried by an internal network.

In all cases, these systems provide for an a posteriori and voluntary triggering of the process, following a fall or a malaise. This therefore assumes that the subject still has the ability and the will to do this.

A variety of remote alarm systems are known in prior art. In particular, portable devices exist under the form of a medallion around the neck, which requires a tightening or traction action to trigger an alarm. Apart from the fact that they are passive systems (requiring voluntary action from the wearer), these devices often produce false alarms, for example during the night, when they are worn and caught in the bedclothes. Furthermore, it is never known whether they are being worn or not.

Movement sensors are also known in prior art, providing information on abnormal nocturnal activity, or position sensor systems equipping beds in certain medical services.

In fact, in order to describe a fall, working from a person's centre of gravity, a cinematic has to be established, that means knowing the initial conditions (weight, height, position), the three accelerations and the three rotations. Such a solution is proposed in the French patent document FR-2760116 which uses two gyros. The trajectory is calculated and an inclinometer provides information about the end of the movement.

It can be carried in a pocket, but it still consumes a significant amount of energy, which is a factor limiting its use for a person in an isolated situation. Furthermore, it can only detect significant falls, and not a "micro-fall" on the patient's bed, or a slow fall, for example along a wall. But it is known that a dependent person, physically limited in movement, looks for supports along a path. Furthermore, in a sitting or lying-down position, a malaise will not be followed by an alarm.

Other systems are known in prior art associating the detection of deceleration at the moment of a fall and a two-directional vocal channel, systems associating protection relative to verticality and evaluation of the kinetic energy of the human body and systems associating an actimetry analysis with a position sensor.

In general, these different techniques are not 100% efficient, but only capable of detecting serious falls, with varying degrees of precision. They have two major inconveniences:

not all falls or malaises are systematically detected, especially when the subject is seated or lying down;
they produce a significant number of false alarms.

Furthermore, non-ambulatory medical monitoring ensembles are known, able to transmit measurements of certain physiological parameters. The most sophisticated use telemedicine. These are complex and expensive systems, reserved for certain types of patients, but are not adapted to elderly persons and/or those with reduced mobility in isolated locations.

Yet again, other types of physiological sensors are known (pulse, breathing, temperature etc.) but they are never associated with decisional processes, and do not enable detection of an abnormal situation such as a fall.

The aim of the invention, in particular, is to overcome these different disadvantages of prior art.

More precisely, one aim of the invention is to provide a device and a method for detecting abnormal situations, particularly falls, with optimum reliability (meaning around 100%). In particular, the aim of the invention is to make it possible to detect all types of falls, even when the wearer of the device is in bed or sitting down, or with the body leaning against a wall.

Another aim of the invention is to provide such a device and such a process which can suppress, or at least greatly diminish, the production of false alarms (due, for example, to a sudden movement, or an inadvertent bang etc.).

In other terms, the aim of the invention is to make it possible to detect abnormal situations both more surely and more efficiently than known techniques.

Moreover, one aim of the invention is to provide such a device which:

is relatively simple and inexpensive to manufacture;
has low energy consumption, and therefore good autonomy;
is not cumbersome, but is ergonomic (meaning that it is not a nuisance for the wearer).

These aims, as well as others which will become clear hereinafter, are attained according to the invention with the aid of a device for detecting abnormal situations, especially falls, in a living being, comprising means for generating an alarm signal representative of an abnormal situation, in function of an analysis of at least one item of activity information and, at least in certain cases, at least one item of physiological information.

BRIEF SUMMARY OF THE INVENTION

Thus, according to the invention, one obtains an efficient and precise definition of abnormal situations, taking into account two types of information.

Evidently it is possible that, in certain situations, the activity information may be sufficient (a sudden fall, for example). In this case, it is not obligatory to take the physiological information into account. Inversely, it can be envisaged that physiological information is recorded and analyzed periodically, even in the absence of any disturbing activity information.

More precisely, the device according to the invention comprises:
means for detecting a potential abnormal situation, supplied by an actimetric system delivering information about activity; and
means for confirming said potential abnormal situation, supplied by at least one physiological sensor delivering physiological information.

As mentioned hereabove, it may involve only one mode for utilizing activity and physiological information, amongst several.

Preferably, in continuous operation mode, only the detection of actimetric information is active, whilst physiological information is determined at regular intervals and/or at the time of a potentially abnormal situation.

This approach makes it possible to produce low energy consumption systems, the physiological information only being obtained and analysed when this is necessary to remove any doubt. In continuous operation mode, only the activity information is followed up.

According to a particular embodiment of the invention, said actimetric system comprises at least one accelerometer. Advantageously, it implements at least two (and generally three) accelerometers, with their outputs summed in such a way as to form a single activity signal, supplying said means for detecting a potential abnormal situation.

The data processing is thus simplified, while still providing high efficiency.

According to another advantageous embodiment of the invention, said actimetric system comprises at least one pressure sensor, also ensuring the detection of physiological parameters. The signal delivered by the pressure sensor is therefore rich in information, and preferably a first separation of variables is carried out, between actimetry and physiological parameters. Part of the information about movement can thus be processed by a non-linear interface and can act to activate the microprocessor following a discontinuous motor activity.

Thus the pressure sensor forms, simultaneously, at least a part of the actimetric system and at least a part of the physiological sensors.

Preferably, the physiological sensor or sensors deliver at least one item of information belonging to the group comprising:
the pulse;
a measurement as a function of the arterial pressure (for example an external pressure as a function of the arterial pressure, modulated by the breathing, the analysis enabling this measurement to be demodulated and the pulse rate to be calculated);
the rhythm and/or breathing airflow;
the temperature (in particular the local cutaneous temperature), and variations and/or combinations of these measurements.

Most of these data can be deduced from the signal delivered by a single pressure sensor. Thus, advantageously, the device according to the invention implements at least one dynamic pressure sensor sensitive to the heart beat of said subject. In particular, one can envisage such a sensor being fitted with an elastic bracelet, making it possible to transmit the heat beat from the inside of the wrist.

Advantageously, the device according to the invention comprises means for measuring information representative of the applied force of said device on the skin of said subject. Furthermore, advantageously, this information makes it possible to verify whether or not the device is being worn (and is held in place adequately).

According to a preferred embodiment of the invention, this is produced in the form of a watch with a bracelet. Thus one obtains a device both practical and discreet.

Advantageously, the device according to the invention comprises a feeler mechanism, or piston, forming an interface between the skin of said subject and at least one physiological sensor. This makes it possible to overcome problems due to displacement or movement of the area applied on the skin of the wearer.

According to another advantageous embodiment of the invention, the device comprises means for generating a local alarm and means for transmission of said alarm to a distant site, after a predetermined delay period, when said alarm has not been invalidated manually by said subject.

Thus, one avoids transmitting false alarms to a distant management site. The wearer himself or herself ensures the control of false alarms.

Advantageously, the device further comprises means for manual activation, transmitting an alarm to a distant site. The wearer can also, even in the absence of automatic detection, warn the monitoring site, for example in the case of a malaise or prior signs of the latter.

According to a preferred embodiment, said manual activation is obtained by pressing strongly on said device, so as to act on said means for measuring information indicative of the applied force.

The implementation is thus very simple, and does not require any supplementary means.

Advantageously, the device according to the invention comprises memory means of at least one model of fall and/or of a series of said physiological measurements.

Preferably, means are provided for displaying at least one of the items of information belonging to the group comprising:
time and date;
physiological information;
lerts;
personalized messages, at a given moment;
information about location.

The device can also comprise at least one photodiode, for transmitting information to processing means for said device and/or to deliver explanative information.

The device for detecting abnormal situations can also operate a microphone, be associated with an anti-fugue system, comprise localization means and/or means for physiological monitoring.

The invention also relates to the method implemented by the device described above. This method comprises, in particular, a stage for generating an alarm signal, representative of an abnormal situation, in function of an analysis of at least one item of activity information and, in certain cases, of at least one item of physiological information.

Preferably, the method comprises the following stages:
detection of a potential abnormal situation, in function of said activity information; and
confirmation or invalidation of said potential abnormal situation, in function of physiological information.

Advantageously, it also comprises the following stages:
generation of a local alarm;
delay period of a defined time length, waiting for an invalidation order from said subject;
transmission of said alarm to a distant site, when said alarm has not been invalidated during said delay period.

BRIEF DESCRIPTION OF THE DRAWINGS

Other characteristics and advantages of the invention will become clearer by reading the following description of a preferred embodiment of the invention, given only as an illustrative and non-limiting example, and the drawings attached among which:

FIGS. 6A and 6B show the different sensors and their environment applied during operation of the device according to the invention, according to two embodiments:

DETAILED DESCRIPTION OF PREFERRED EMBODIMENTS

The aim of the invention is thus a device for detecting abnormal situations in a subject, falls in particular. This device and the corresponding method are more reliable and more precise that systems known in prior art, in particular because they combine, at least when necessary, actimetric and physiological information, as shown by the general block diagram of FIG. 1.

Figure 1:
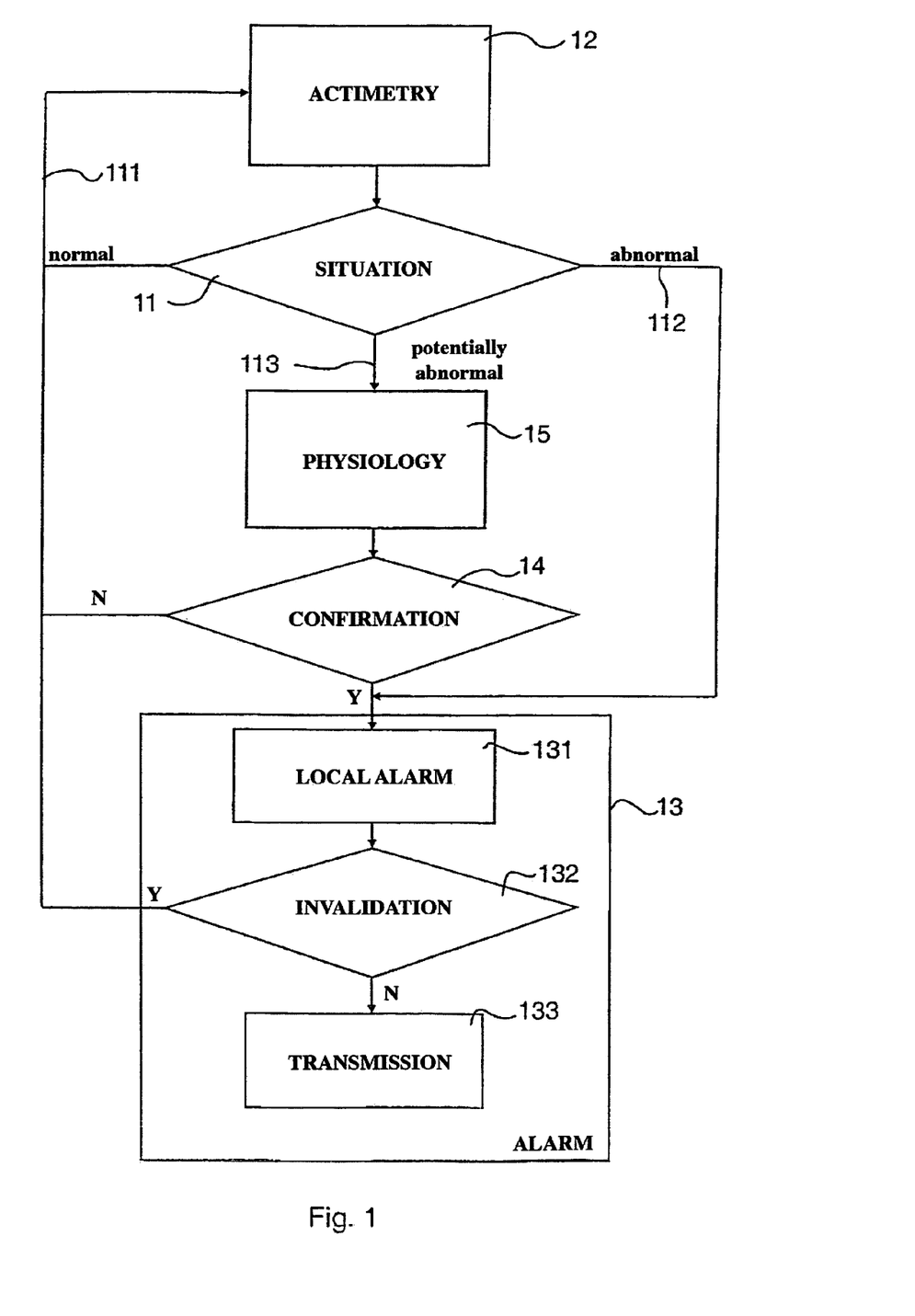
FIG. 1 is a general block diagram illustrating the principle of the invention in the event of a fall.

The analysis of the actimetric situation of the patient, in function of the actimetric information 12 can be of three types:

normal 111: then only the actimetric sensors function;

evidently abnormal 112: in this case one passes directly to stage 13 for generating an alarm;

potentially abnormal 113: this is the usual case where a significant movement has been detected, without being certain whether it involves a fall (this case is more frequent when the movement detection thresholds are low, so as to be able to detect "micro-falls").

In the latter situation 113, a supplementary stage 14 is implemented for confirmation or invalidation of the normality of the situation, in function of actimetric information 12. If the wearer can move, he or she can activate an alarm manually. In the opposite case, the physiological information 15 is taken into account. In the case of invalidation, one returns to the normal situation 111. In the opposite case, one passes to the stage of generating an alarm. It is evident that the physiological data can be subject to regular measurement, independent of movement detection, and if necessary provoke the triggering of an alarm, for example in the case of a cardiac problem (even without a fall . . . ).

The actimetric and physiological information can also be used in parallel, or in any other satisfactory way.

According to another advantageous embodiment of the invention, the generation of alarms 13 takes place in two stages, so as to avoid the generation of false alarms, and therefore needless interventions by the persons in charge of telemonitoring. Therefore, a local alarm 131 is generated first of all, for example under the form of a sound signal.

The wearer then has a predetermined time delay, for example several tens of seconds, to intervene, cancel the alarm if he or she considers that the situation does not require an intervention. In the case where the alarm is cancelled 132, one returns to normal mode. In the contrary case, an alarm is transmitted, 133, to the telemonitoring site.

The device according to the invention, advantageously worn as a watch, thus comprises an ensemble of motricity sensors, making it possible to detect accelerations of the wrist. These measurements, an example being given in FIG. 2 (21, 22 and 23 with accelerations respectively along axes X, Z and Y) are thus in the forefront for detecting a critical energy level. In fact, the pass band of accelerations during a fall is comprised between 0.5 Hz and 6 Hz, considered as a narrow band.

Figure 2:
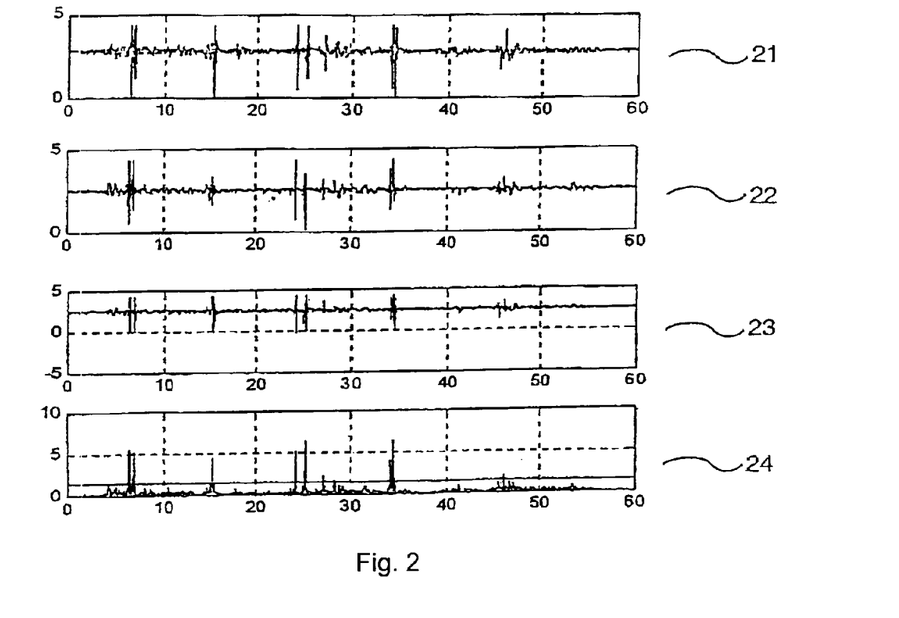
FIG. 2 is an example of signals delivered by the accelerometers in the event of a fall, and of their summing.

In order to optimise energy consumption, one assimilates the rectified signals 21, 22 and 23 summed and filtered in low-pass to the energy input, to obtain the signal 24, which acts by stimulating the calculation means of the device.

According to an advantageous variant of the invention, the motricity sensors can be replaced by a single pressure sensor, which also ensures detection of the physiological parameters.

In the following seconds, energy measurements are carried out and compared with a model of a fall, according to the algorithm described hereinafter. After stimulation, the measurements from the accelerometers (or from the pressure sensor) after analysis of a part of the actimetric information processed by a non linear interface) are converted into energy. The comparison or the thresholding takes place relative to a model, that is an ensemble of successive values representing an evolution with time (for example the form of the wave after an impact), and not relative to a single threshold value.

This fall can be relative, meaning that the center of gravity of the human body remains almost unvaried. In this case, the comparison can prove to be difficult. This is the reason why the evolution of certain physiological parameters (pulse, breathing. . .) is observed as indicator of an abnormal situation.

Figures 3, 5:
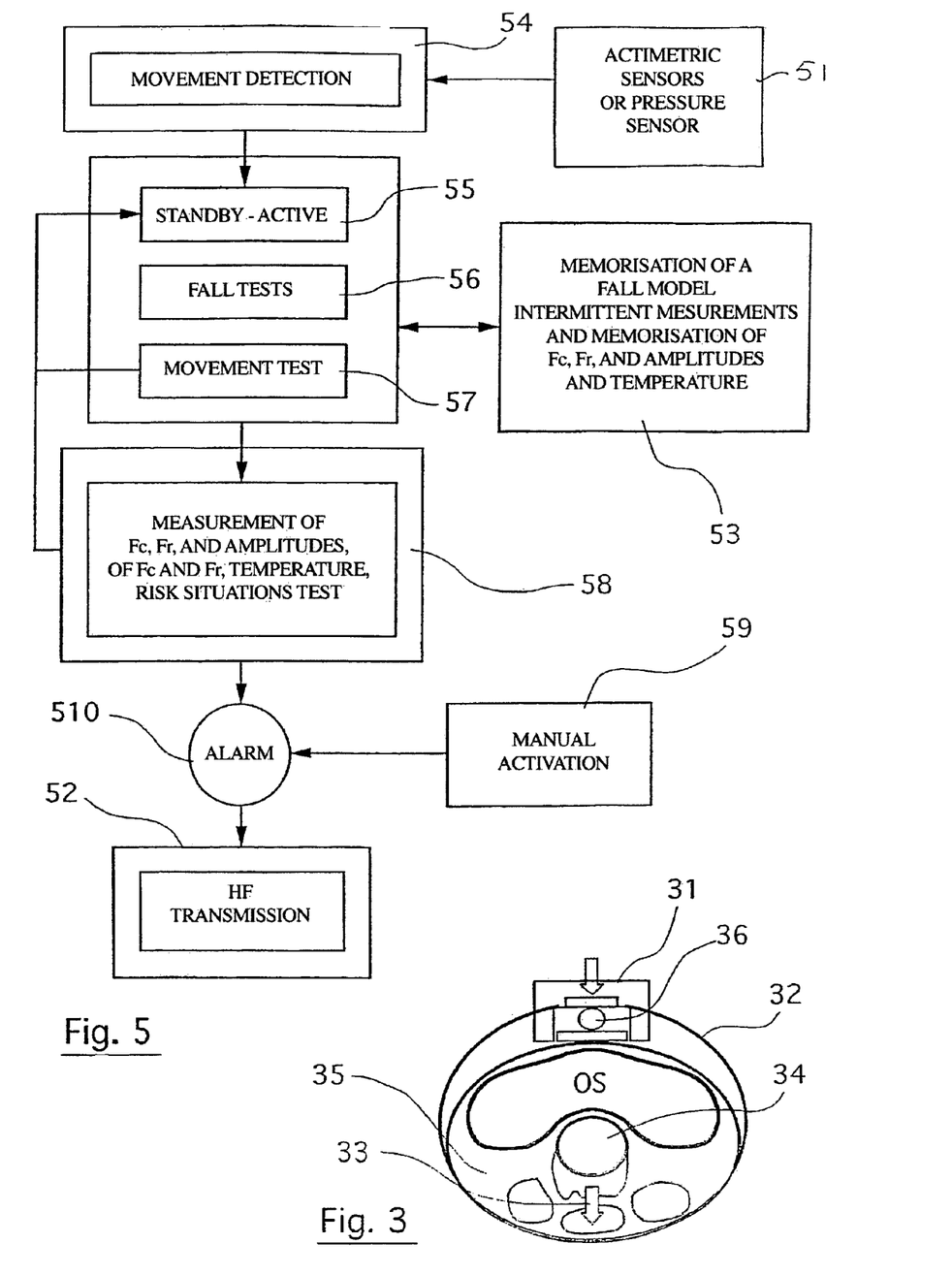
FIG. 3 shows the transfer principle of the heart beat to the device according to the invention, produced under the form of a bracelet watch.
FIG. 5 is a block diagram showing the functionalities of the device according to the invention.

As shown in FIG. 3, the watch housing 31 is held on the wrist with the aid of an elastic bracelet 32, similar to that of a normal watch. The heart beat 33 crosses the vessels 34, the muscle, the tissues 35 and the skin and then propagates through the bracelet 32, creating a stress on the sensor 36, described in more detail hereinafter.

Figure 4A:
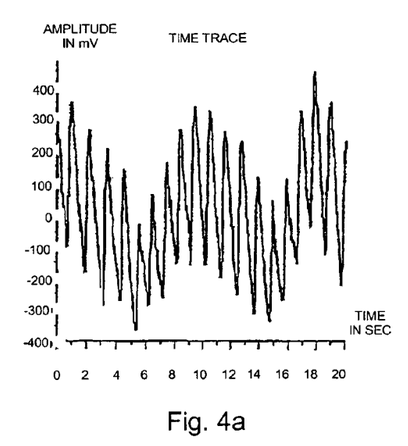
FIGS. 4*a* and 4*b* show an example of cardiac waves modulated by breathing, in the time domain and in the frequency domain.
Figure 4B:
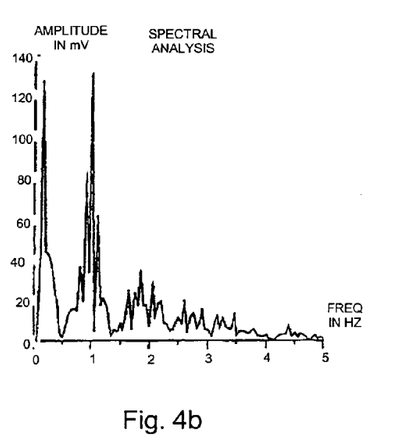

Thus, the accessible physiological parameters at wrist level are the image of the heart beat, FIGS. 4*a* and 4*b* providing examples respectively of the time trace and the spectral analysis corresponding to a cardiac wave modulated by the breathing, in the case of a sinus arrhythmia in a male 35 years of age. From these signals, it is possible to deduce the pulse rate and respiration frequency, and if necessary the arterial pressure.

By placing a temperature sensor very close to the skin, it is also possible to obtain the local temperature (biased relative to the temperature of the human body) from which the temperature variation can be deduced. Without any movement, these parameters are memorised, the system being self-learning.

After a fall or a malaise, the subject may be physically immobilised. In this case, the body temperature lowers. This parameter can be discriminatory, if the variation of body temperature is significant over a sufficient length of time.

The historic of the physiological parameters after the fall is retraced, in the hypothesis that it is not immediately detected (potential abnormal situation). In fact, it is a function of the pathology causing the fall.

However, if the person is blocked, the following variants can be discovered:

pulse: bradycardia or tachycardia;

breathing: higher rate due to the state of stress, then becoming regular, and then observation of breathing pauses;

arterial pressure: able to vary in one direction or the other (increase or decrease depending on the cause);

temperature change: by extrapolating the reaction of the body of a person in sleep situation to that of an immobilized person, and knowing that man is endothermic since only the internal temperature is constant, it is possible to assume that the thermo-regulation mechanism ensures maintenance of this endothermia, despite ambient conditions which can be very variable. However, skin temperatures are not uniform: the lowest temperatures are those of the hands and then the feet (28 to 31° C.) when the temperature of the head, the highest, is of the order of 34 to 35° C.

FIG. 5 shows the principle functions of the device according to the invention.

In continuous operation mode, only the actimetric means 51 are active. The microcontroller is on standby, as well as the HF transmitter. Intermittently, measurements are taken of the heart beat frequency (Fc) and then the breathing frequency (Fr) and the temperature, and the respective amplitudes, which are memorised (53) to follow the evolution of these measurements, and eventually to be able to affirm that the subject is no longer in a normal situation.

In the case where the motricity level is exceeded, (deduced from a movement 54), the microcontroller is activated (55), and acquisition begins, with the aim of sensing the motricity signals and of detecting whether or not there has been a fall (56), beginning from a memorised algorithm (53).

Then the preceding physiological parameters are acquired (58), for example for 30 seconds, calculations are made and an overrun test started.

Next, a movement test 55 is implemented, to verify whether or not the wearer can move. In this case, manual action 59 on the alarm is possible, as well as transmission of an alarm when the device is not worn or is not correctly tightened.

The alarm 510 is transmitted via transmission means HF 52.

Advantageously, the transmission indicates the type of alarm:

watch not worn;

tightness insufficient;

physiological parameters outside the threshold;

fall;

manual activation.

Figure 6A:
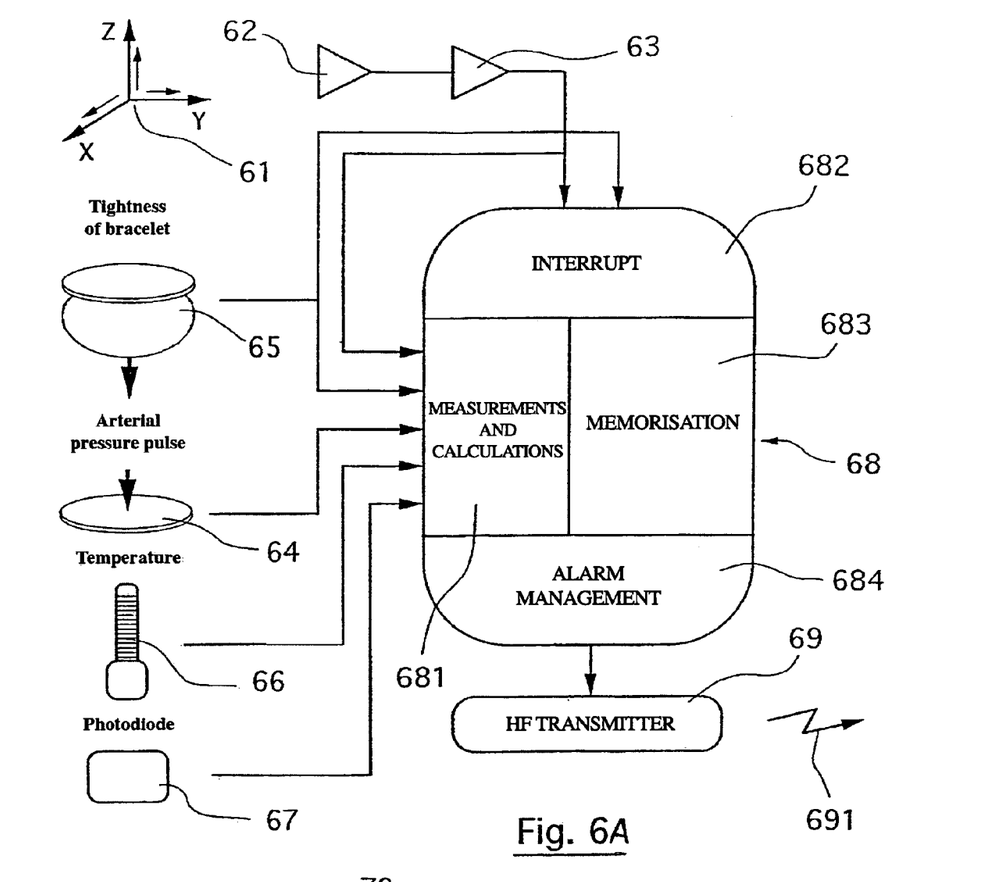
FIG. 6A: implementation of three piezoelectric sensors.
Figure 6B:
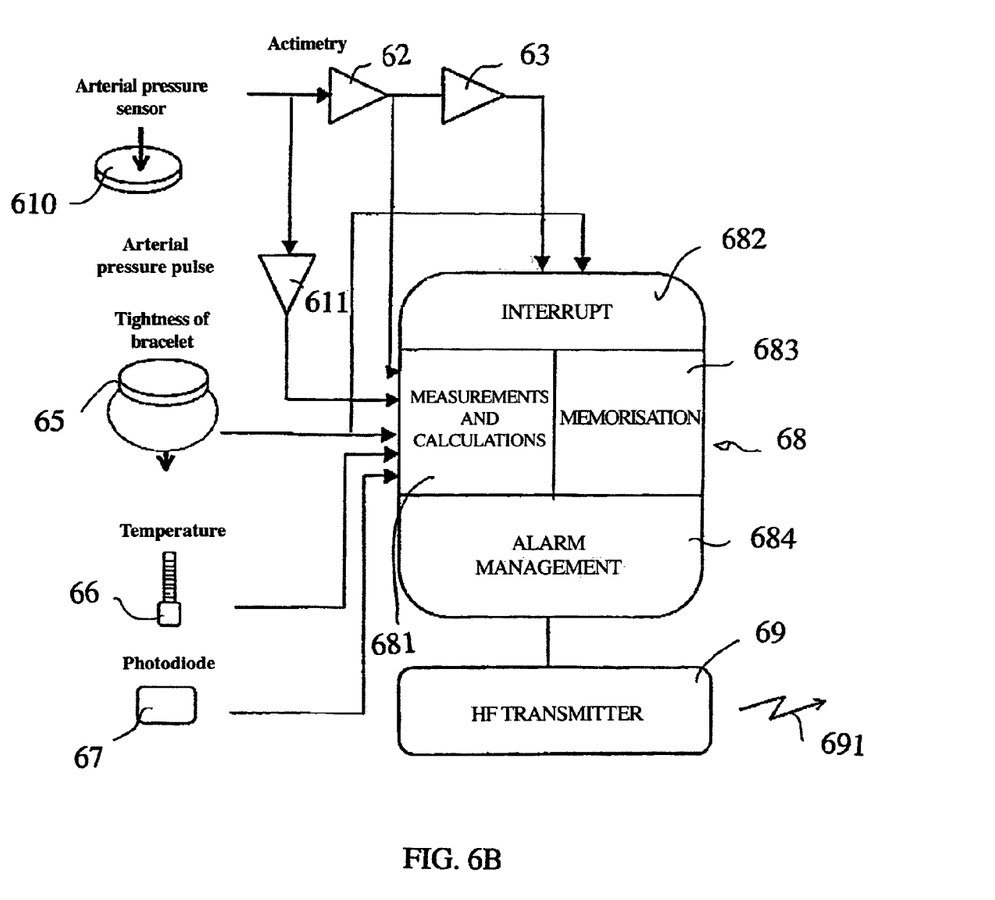
FIG. 6B: implementation of a pressure sensor.

FIGS. 6A and 6B show the environment of the sensors implemented, respectively in the cases:

6A: implementation of three piezoelectric sensors;

6B: implementation of one pressure sensor.

In the case of FIG. 6A, the three accelerations are for example picked up by an integrated or modular 3D 61 accelerometer, for example of the ACH 04-08-05 type manufactured by the AMP company (registered trademark) or any equivalent type, with a sensitivity of 2 mV/g in the pass band 0.5 Hz to 10 Hz. They are followed by a summing amplifier 62 (see FIG. 2), with an amplification of gain 50 and a thresholding 63 in the corresponding pass band.

The detection of cardiac pressure is carried out using a piezoelectric sensor 64, with a disc shape, (diameter $\theta=16$ mm, e=0.5 mm) using the direct piezoelectric effect (material PZT PIC 155; manufactured by PI CERAMIC (registered trademark)). The value of the capacity for 1 Hz is 8.65 nF. When charged under an equal capacity in parallel, with a resistive charge of 33 M$\Omega$, the split frequency is 0.6 Hz and the sensitivity is 54 mV/N. A transimpedance stage ensures the liaison with an amplifier with gain 500 and pass band 0.5-3 Hz for a heart beat delivering $\frac{1}{100}$N at the level of the sensor, obtaining an output signal of 400 mV peak to peak amplitude.

This sensor can also give the acceleration image along the axis Z.

In the case where a pressure sensor 610 is applied (FIG. 6B), advantageously it can be a piezoelectric sensor such as that described above. The environment of the pressure sensor comprises a non-elastic but deformable resin forming a volume between the sensor itself and a flexible membrane linked to the piston.

Under the action of a longitudinal movement, one discovers the same effect as that caused by a heart beat. Under a transversal action, the displacement of the watch housing brings about a variation in the length of the bracelet or a variation of stress detected by the pressure sensor. The signal transmitted by the pressure sensor is therefore very rich in information (actimetric information and physiological parameters). The operational amplifiers used are of the very low energy consumption type, for example MAX 418 amplifiers of the MAXIM company (registered trademark).

The tightness of the bracelet is detected by a resistive sensor 65 of the type FSR 152-NS, a flat semiconductor sensor coated with a polymer. When integrated into a stage with operational amplifier, it is possible to discriminate between 4 output levels which are:

higher than 1 V: watch not being worn;

between 0.15 V and 0.9 V: watch being worn;

lower than 0.09 V: very tight, voluntary and serving as manual alarm button.

It is to be noted that each of the stages is separated from the next by a blank zone, making it possible to make the analysis secure.

In order to improve detection of the presence of the manual alarm, a level stability test is carried out.

It is also possible to use a Motorola sensor (registered trademark) MX 2300, which improves discrimination between situations.

The temperature sensor 66 can be a semiconducting sensor LM 62 manufactured by National Semiconductor (registered trademark). Its resolution is 0.2°. Advantageously, it can be set in the feeler mechanism, or piston, separated from the skin by about 1 mm.

The photodiode sensor 67, for example of the type BPW 34 from SIEMENS (registered trademark), acts to transmit information by means of calculations 681 (initialisation, tests . . . ) and can also provide information about the ambient lighting.

The micro-controller 68 can be decomposed, operationally, into:

means for management of interrupts 682, supplied by actimetric information and information from the tightness of the bracelet;

means for measurement and calculations 681 supplied by actimetric, tightness, arterial pressure, temperature and photodiode information;

memory means 683;

means for alarm management 684.

In the case of FIG. 6B, the means 681 and 682 are supplied directly by the arterial pressure sensor 610 via amplifiers 62, 63 and 611 (which provide a difference in arterial pressure).

The management means of alarms 684 act on the transmitter HF 69, to set off the alarm 691, for example to a fixed base.

Figure 7:
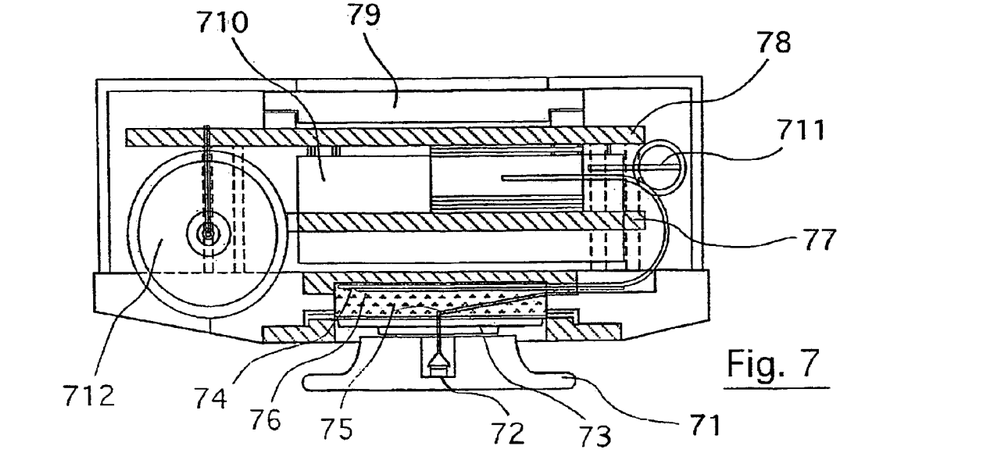
FIG. 7 shows a cross section of an embodiment according to the invention.

FIG. 7 describes the assembly of different sensors and electronics integrated inside the watch housing, in cross section.

A piston 71 is provided to come into contact with the wearer's skin. It contains a temperature probe 72. A membrane 73, attached to the piston 71, ensures the transfer of the heart beat (or of a longitudinal movement in the case of a pressure sensor embodiment), enabling a variation of perpendicularity between the piston 71 and the sensors. The liaison between the sensors and the piston is made by silicon gel 75, decoupling the assembly mechanically.

The piezoelectric heart beat detection sensor 76 is attached to the tightness sensor of the bracelet 74. Thus, there exists a pre-stress on the piezoelectric material, enabling detection of small impulses.

The electronics are constituted of printed circuits 77 and 78. Evidently, this can be reduced to a single printed circuit. The time display, and any other information, is restored by the display 79, for example of the liquid crystal type. The alarms are carried via the transmitter 710 and the antenna 711. The energy source is a battery 712, ensuring autonomy for the device of more than one year. The latter is held against the wrist by an elastic bracelet (not shown).

The sealing means are not shown either, but are chosen in such a way as the ensure sealing against running water. The materials which are used and which are in contact with the skin are not harmful and more generally are not dangerous for permanent wear of the watch.

The electronics comprise two principle functions, which are the environment of the sensors (already described relative to FIG. 6) and the means for calculation and emission. The calculation means embarked can be produced by microcontrollers with very low energy consumption, of the MSP family from Texas Instruments (registered trade mark) or of the XE 88xx family from XEMICS (registered trademark). These microcontrollers have means for high precision analog measurement (more than 12 bits), time bases, drivers for liquid crystal displays (display of time and certain alarms), an adequate memory programme and digital links with an HF transmitter of the FM type, with a range of 60 m in a free field.

Before describing the monitoring algorithm in more detail, the following three points should be noted:

- unnecessary activation of false alarms is a major problem for any automatic detection system. A system generating a high level of false alarms is a system which will be quickly abandoned. To overcome this disadvantage, an alarm with automatic activation is to be systematically validated, within a certain time period, by the wearer, before being transmitted. When this time period expires, transmission of the alarm is obligatory, because this indicates that the wearer is incapable of reacting and consequently is in difficulty. Therefore, the wearer of the device must deal with false alarms, and not the emergency service;
- a fall followed by inactivity is an disturbing situation. This aspect is integrated in order to take a final decision (alert or non-alert).
- autonomy is a crucial parameter for an ambulatory system. It has therefore been taken into account from the very beginning of the design of the device. The monitoring of signals from the accelerometers or from actimetric information is ensured by an analog device of low energy consumption. The role of this device consists, in the case where the threshold is exceeded (activity considered to be abnormal), of reactivating the microcontroller managed in standby/active mode, thus avoiding any superfluous energy consumption. An analysis of the parameters is then carried out to determine whether the situation is critical or not. Monitoring of the physiological parameters is carried out periodically in order to detect any anomaly.

Figure 8:
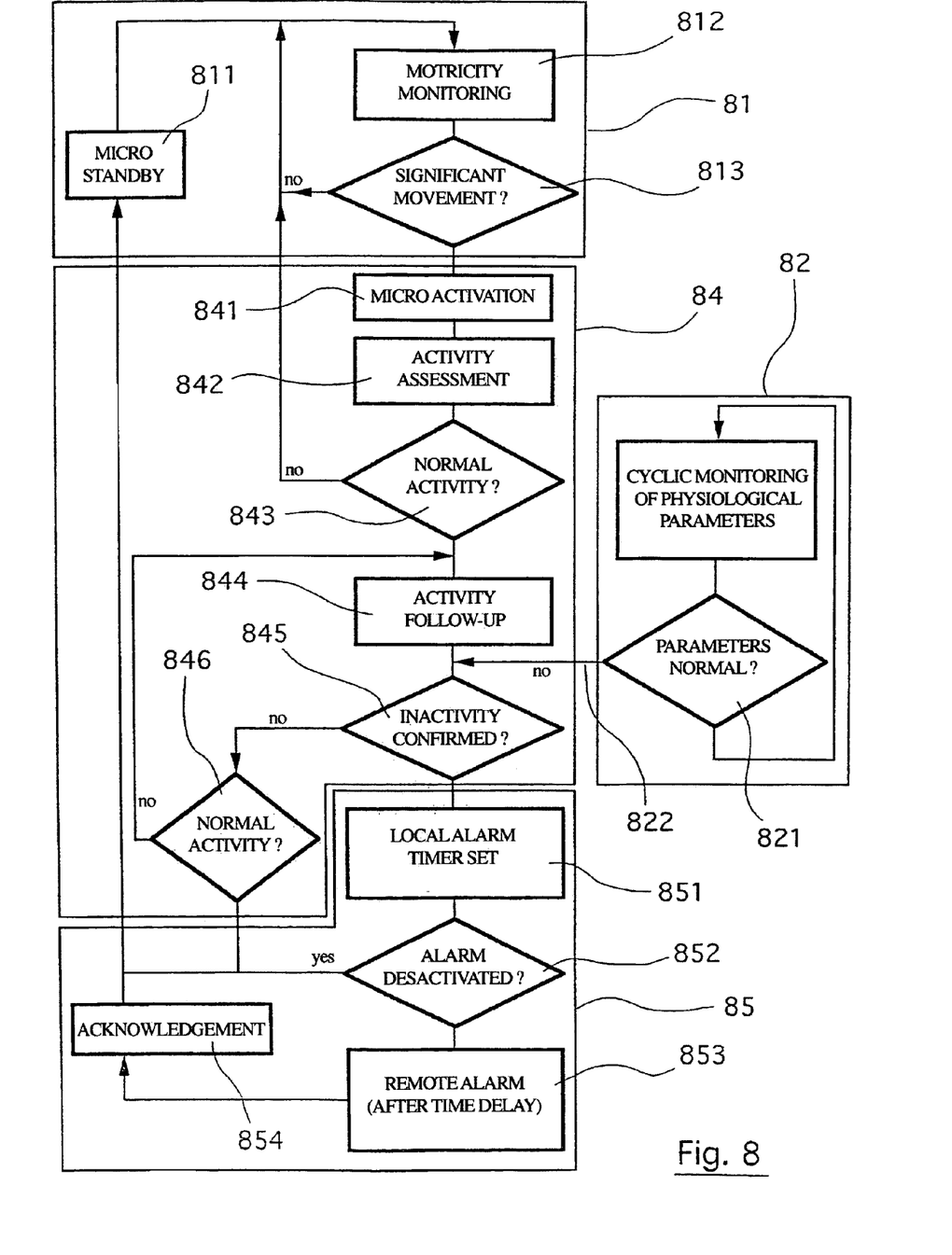
FIG. 8 is a detailed flow chart of the monitoring method according to the invention.

FIG. 8 shows the monitoring flow chart.

In normal and continuous mode conditions, the passive monitoring mode 81 is applied by the analog device. The microcontroller is in standby 811. Motricity is monitored 812, and one remains in this mode as long as no significant movement is detected 813.

At regular intervals; a cyclic monitoring 82 is implemented using physiological parameters. As long as these parameters are normal 821, no action is taken.

When a significant movement is detected 813, one passes to the active monitoring mode 84 through the analog device. The micro is activated 841, and then the activity is assessed 842. If the activity is considered to be normal 843, one returns to the passive monitoring mode. In the opposite case, one passes to activity follow-up 844, taking into account the physiological parameters 822. If there is confirmation of inactivity, one passes to the alarm system mode 85. In the opposite case, one verifies whether or not the activity is normal 846. If the response is negative, one returns to the stage 844 for activity follow-up. In the opposite case, the micro returns to standby 811.

The alarm mode comprises first and foremost a local alarm 851 comprising setting of timing. If the alarm is deactivated 852 during this time, one returns to the normal situation and the micro returns to standby 811. On the contrary, an alarm is transmitted 853, after the time delay has expired. After confirmation of the alarm 854, the micro returns to standby 811.

Evidently, one can envisage many variants, as complement and/or as option to the device according to the invention.

In particular, one can use a display, liquid crystal for example, to display information such as the time, or personalised messages (taking medicines, appointments, activities . . . ).

Moreover, considering that the pass band of the HF transmitter is sufficient, a microphone can be integrated into the watch to transmit the voice. It is also possible to envisage means for receiving vocal or other information.

An anti-fugue system can be set up, for example by transmission of an HF signal every fifteen minutes. A function for passing detection can also be integrated via the photodiode, since the pass to be detected is equipped with a light emitter. The cyclic emission of the HF signal can also make it possible to monitor the quality of transmission, and thus to make the system secure.

Continuous information about the pulse, the temperature and the tightness of the bracelet, when using a linear pressure sensor, breathing parameters . . . , make it possible to provide a home monitoring system, in the form of a convivial ambulatory system.

Finally, it is possible to envisage associating localisation means (GPS) and/or basic functions of a mobile phone, to increase the autonomy relative to distance and/or to constitute a complete anti-fugue system.

The invention claimed is:

1. Device for detecting falls of a living subject, comprising:
   a pressure sensor, delivering a signal representative of a pressure from said living subject;
   means for separating information present in said signal representative of a pressure, delivering at least one item of information about activity and at least one item of physiological information; and
   means for processing of said at least one item of physiological information to detect a potential fall of the living subject, and
   means for providing an invalidatable alarm which at least one item of information about activity can invalidate.

2. Device according to claim 1, wherein said means for processing comprise:
   means for detecting a potential abnormal situation, supplied by said at least one item of physiological information;
   means for confirming said potential abnormal situation, supplied by said at least one item of information about activity;
   means for delivering information of a confirmed abnormal situation; and
   means for generating an alarm signal.

3. Device according to claim 1, wherein, in a continuous operation mode, only detection of at least one physiological information is active, and in that at least one activity information is determined at regular intervals and/or in the presence of a potential abnormal situation.

4. Device according to claim 1, wherein said at least one item of physiological information belongs to the group comprising:
   the pulse;
   a measurement as function of the arterial pressure;
   the rhythm;
   the breathing airflow;
   variations of these measurements; and
   combinations of these measurements.

5. Device according to claim 1, and further comprising means for measuring one item of information representative of the application force of said device on the skin of said subject, said application force being used to verify that said device is worn correctly.

6. Device according to claim 1, wherein the device is made in the form of a bracelet watch.

7. Device according to claim 1, and further comprising means for generating a local alarm and means for transmitting said alarm to a distant site, after a predetermined delay period, when said alarm has not been manually invalidated by said subject.

8. Device according to claim 1, and further comprising means for manual activation, transmitting an alarm to a distant site.

9. Device according to claim 1, and further comprising means for memorization of at least one model of fall.

10. Device according to claim 1, and further comprising display means for at least one of the items of information belonging to the group comprising:
    time and date;
    physiological information;
    alerts;
    personalized messages, at a given moment; and
    information about location.

11. Device according to claim 1, and further comprising at least one photodiode, for the transmission of information to the processing means of said device.

12. Device according to claim 1, and further comprising a microphone.

13. Device according to claim 1, wherein the device is associated with an anti-fugue system.

14. Device according to claim 1, and further comprising means for physiological monitoring.

15. Device according to claim 1, and further comprising means for memorization of a series of said physiological measurements.

16. Device according to claim 1, and further comprising at least one photodiode, for delivering lighting information.

17. Device according to claim 1, and further comprising a temperature sensor.

18. Device for detecting falls of a living subject, comprising:
    a pressure sensor, delivering a signal representative of a pressure from said living subject;
    means for separating information present in said signal representative of a pressure, delivering at least one item of information about activity and at least one item of physiological information; and
    means for processing of said at least one item of information about activity to detect a potential fall of the living subject, and
    means for providing an invalidatable alarm which at least one item of physiological information can invalidate.

19. Device according to claim 18, wherein said means for processing comprise:
    means for detecting a potential abnormal situation, supplied by said at least one item of information about activity;
    means for confirming said potential abnormal situation, supplied by said at least one item of physiological information;
    means for delivering information of a confirmed abnormal situation; and
    means for generating an alarm signal.

20. Device according to claim 18, wherein, in a continuous operation mode, only detection of at least one activity information is active, and in that at least one physiological information is determined at regular intervals and/or in the presence of a potential abnormal situation.

21. Device according to claim 18, wherein said at least one item of physiological information belongs to the group comprising:
    the pulse;
    a measurement as function of the arterial pressure;
    the rhythm;
    the breathing airflow;
    variations of these measurements; and
    combinations of these measurements.

22. Device according to claim 21, wherein said pressure sensor comprises at least one dynamic pressure sensor sensitive to the heart beat of said subject.

23. Device according to claim 18, and further comprising means for measuring one item of information representative of the application force of said device on the skin of said subject, said application force being used to verify that said device is worn correctly.

24. Device according to claim 18, wherein the device is made in the form of a bracelet watch.

25. Device according to claim 18, and further comprising means for generating a local alarm and means for transmitting said alarm to a distant site, after a predetermined delay period, when said alarm has not been manually invalidated by said subject.

26. Device according to claim 18, and further comprising means for manual activation, transmitting an alarm to a distant site.

27. Device according to claim 18, and further comprising means for memorization of at least one model of fall.

28. Device according to claim 18, and further comprising display means for at least one of the items of information belonging to the group comprising:
time and date;
physiological information;
alerts;
personalized messages, at a given moment; and
information about location.

29. Device according to claim 18, and further comprising at least one photodiode, for the transmission of information to the processing means of said device.

30. Device according to claim 18, and further comprising a microphone.

31. Device according to claim 18, wherein the device is associated with an anti-fugue system.

32. Device according to claim 31, and further comprising means for localization.

33. Device according to claim 18, and further comprising means for physiological monitoring.

34. Device according to claim 1, and further comprising means for memorization of a series of said physiological measurements.

35. Device according to claim 1, and further comprising at least one photodiode, for delivering lighting information.

36. Device according to claim 1, and further comprising a temperature sensor.

37. Method for detecting falls in a living being, using at least one item of information about activity and at least one item of physiological information, comprising:
measuring at least a pressure from said living being, using at least one pressure sensor delivering one signal representative of a pressure; separating information present in said signal representative of a pressure, and delivering at least one item of information about activity, representative of the activity of said living being, and at least one item of physiological information; and
processing said at least one item of information about activity and said at least one item of physiological information to detect a potential fall in a living being, and providing an invalidatable alarm which the processed physiological information can invalidate.

38. Method according to claim 37, and further comprising:
detecting a potential abnormal situation, in function of at least one item of activity information;
confirming or invalidating said potential abnormal situation, in function of at least one item of physiological information; and
generating an alarm signal, representative of the confirmed abnormal situation.

39. Method according to claim 37, and further comprising:
generating of a local alarm;
awaiting of an invalidation order from said subject, during a delay period of a predefined time length;
transmitting said alarm to a distant site, when said alarm has not been invalidated during said delay time period.

40. Method according to claim 37, wherein at least one of said items of information is analyzed relative to a model formed from an ensemble of successive measurements representative of evolution with time.

* * * * *